US00PP37020P2

(12) United States Plant Patent
Huber

(10) Patent No.: US PP37,020 P2
(45) Date of Patent: Oct. 14, 2025

(54) ***DAHLIA* PLANT NAMED 'LeeAnn'S WL186B'**

(50) Latin Name: *Dahlia hybrida*
Varietal Denomination: LeeAnn's WL186B

(71) Applicant: Coseytown Flowers llc, State Line, PA (US)

(72) Inventor: LeeAnn Huber, Greencastle, PA (US)

(73) Assignee: Coseytown Flowers llc, State Line, PA (US)

( * ) Notice: Subject to any disclaimer, the term of this patent is extended or adjusted under 35 U.S.C. 154(b) by 0 days.

(21) Appl. No.: 18/999,464

(22) Filed: Dec. 23, 2024

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Dahlia* plant named 'LeeAnn's WL186B' is disclosed, characterized by a strong, upright growth habit, combined with free branching and early flowering. Inflorescences are held above the foliage canopy. Flowering stems have an above average strength with a firm blossom attachment. Flower color is warm salmon with a distinct red picotee on the ray florets. Inflorescences have strong postproduction quality. The new variety is a *Dahlia* typically produced for cut flower purposes, or garden or landscape.

2 Drawing Sheets

Latin name of the genus and species: *Dahlia hybrida.*
Variety denomination: 'LeeAnn's WL186B'.

BACKGROUND OF THE INVENTION

The new *Dahlia* cultivar is a product of a planned breeding program conducted by the inventor, in Greencastle, Pennsylvania. The objective of the breeding program was to produce new *Dahlia* varieties that excel in outdoor conditions, produce cut flowers and are suitable for container gardens.

Seed from various *Dahlia hybrida* varieties was bulk collected by the inventor during 2014 and planted during 2015. 'LeeAnn's WL186B' was intentionally selected from the seedlings that resulted based on the criteria of stem length and strength, upright growth habit, inflorescence attachment, ray floret count, and inflorescence color.

Asexual reproduction of the new cultivar was first performed by tubers by the inventor in Greencastle, Pennsylvania in the Spring of 2016 and has shown that the unique features of this cultivar are stable and reproduced true to type in successive generations.

SUMMARY OF THE INVENTION

The cultivar 'LeeAnn's WL186B' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LeeAnn's WL186B'. These characteristics in combination distinguish 'LeeAnn's WL186B' as a new and distinct *Dahlia* cultivar:

1. Strong, upright growth habit.
2. Free branching.

3. Early flowering.
4. Inflorescence blooms at and above the leaf canopy
5. Great postproduction inflorescence quality
6. Above average stem strength.
7. Firm inflorescence attachment.
8. Warm salmon inflorescence color with a distinct red picotee on the ray florets.

Parent varieties cannot be identified.

COMMERCIAL COMPARISON

Plants of the new cultivar 'LeeAnn's WL186B' are comparable to the variety *Dahlia* 'Rawhide', unpatented. The two *Dahlia* varieties are similar in most horticultural characteristics; however, the new variety 'LeeAnn's WL186B' differs in the following:

1. Inflorescences of the new variety have more ray florets than inflorescences of this comparator.
2. Ray florets of 'LeeAnn's WL186B' are narrower in width and exhibit an obtuse floret apex, whereas 'Rawhide' is decidedly more rounded at the end of the ray floret apex.
3. Plants of 'LeeAnn WL186B' bloom 3-4 weeks earlier than 'Rawhide' in a field grown environment.

BRIEF DESCRIPTION OF THE PHOTOGRAPHS

Figure 1:
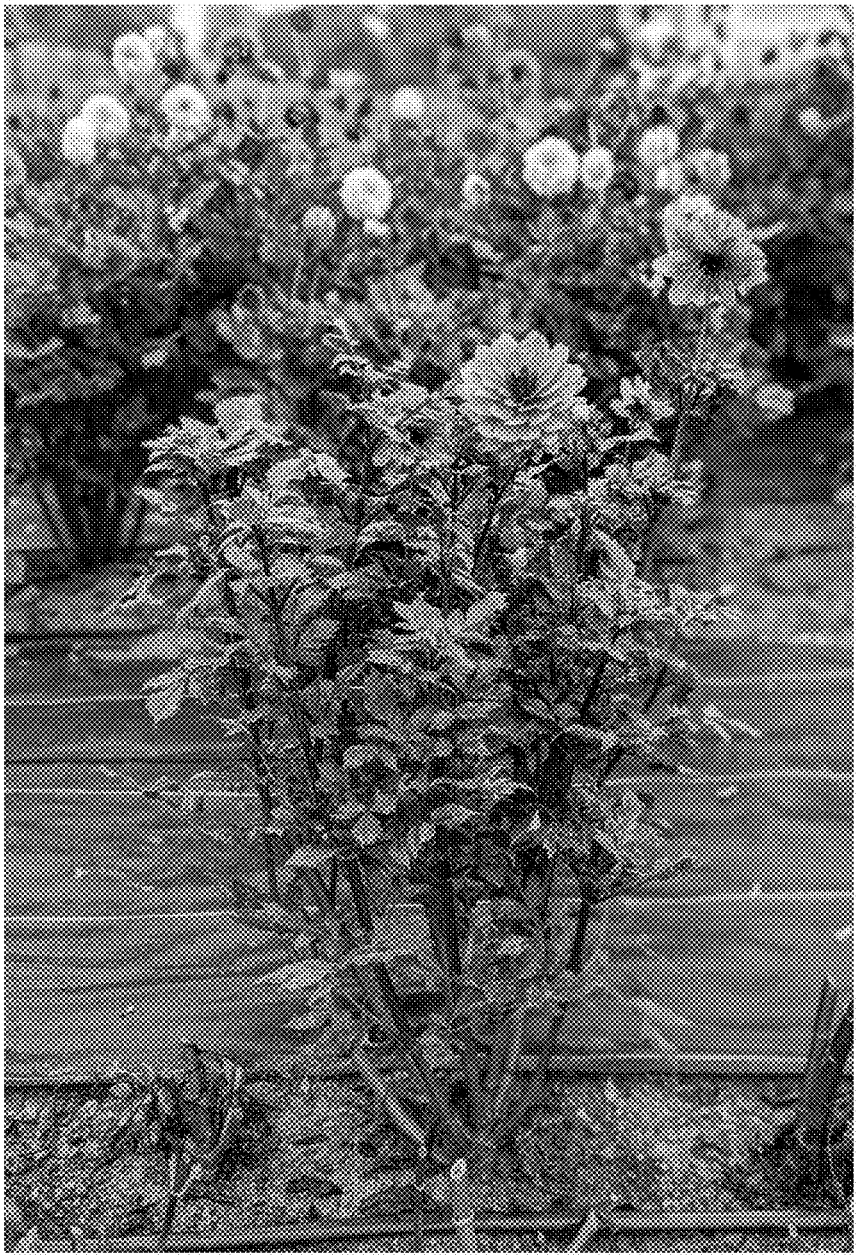
Figure 2:
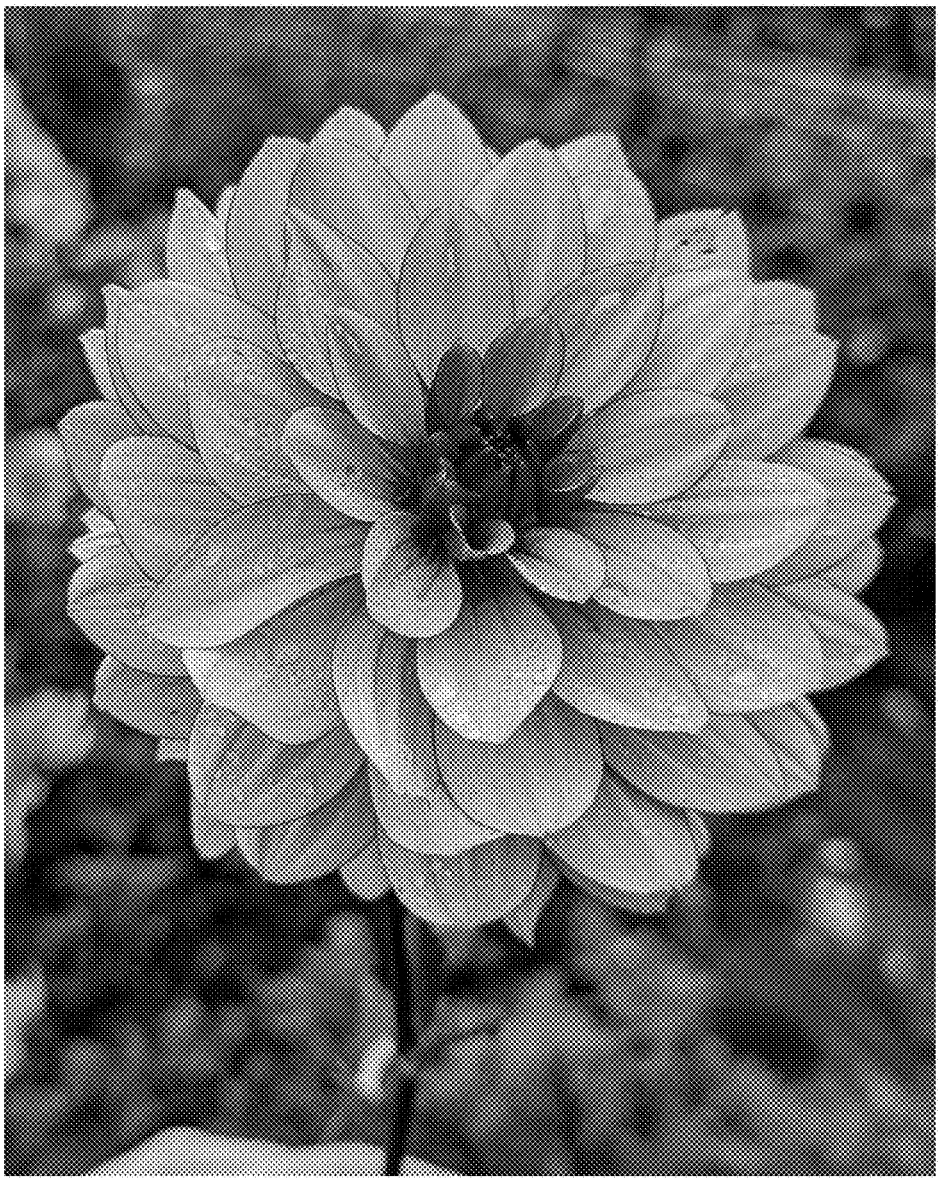

The accompanying photograph in FIG. 1 illustrates in full color a typical flowering plant of 'LeeAnn's WL186B' grown outdoors, in the ground under cut flower production conditions. Age of the plant photographed is approximately 20 weeks from a tuber. Bright green spots and blotches are visible. This discoloration is due to excessive rain(10 straight days) which caused some foliar fungal infection as well as nitrogen deficiency, resulting in these spots. FIG. 2 illustrates a close-up of a typical inflorescence. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society RHS Colour Chart 2015 except where general terms of ordinary dictionary significance are used. The following observations and measurements describe 'LeeAnn's WL186B' plants grown outdoors in Greencastle, PA. Measurements and numerical values represent averages for average plants grown in production cut flower rows. The average growing season for outdoor cut flower production runs from May through mid-October or 24 weeks. The terminal bud is pinched off the dahlia around 4-6 weeks of age. The photographs and descriptions were taken when plants were about 140 days or about 20 weeks old.

Botanical classification: *Dahlia hybrida* 'LeeAnn's WL186B'.

PROPAGATION

Type of propagation typically used: Vegetative terminal cuttings or tubers.

Time to initiate roots, spring: About 5-7 days at 18° C.

Time to produce a rooted young plant, spring: about 21-25 days for roots to fill a 50 count tray cell.

Root description: Freely branching, fine rootlets with canescent hair.

PLANT

Plant Type: Herbaceous flowering perennial.

Growth Habit: Upright growth habit that branches freely producing numerous strong stalks holding inflorescences above foliage. Vigorous growth and regrowth after continuous inflorescence harvesting. The plant does not need mechanical support during the growing season. Inflorescences occur above the leaf canopy. Branch strength is exceptional.

Height: 91 cm.

Plant Spread: 43 cm.

Lateral Branch:

- *Length*.—16inches (about 41 centimeters).
- *Diameter towards base*.—13-14 mm.
- *Diameter towards apex*.—12 mm.
- *2nd internode length*.—About 49 mm.
- *Angle of Lateral Branch from plant center*.—About 35°.
- *Aspect*.—Erect to somewhat outwardly spreading.
- *Branch Strength*.—Exceptional, no flex or give.
- *Texture*.—Smooth, glabrous with longitudinal sulcate grooves.
- *Color*.—Upper and lower side, Greyed-Purple N186 C.

FOLIAGE

Leaf:

- *Shape*.—Ovate.
- *Apex*.—Apiculate.
- *Base*.—Attenuate.
- *Arrangement*.—Opposite. Single or compound with 3 or 5 leaflets.
- *Length*.—Single leaves: About 70 mm. Compound leaves with three leaflets: About 80 mm. Compound leaves with five leaflets: About 170 mm.
- *Width*.—Single leaves: about 40 mm. Compound leaves with three leaflets: about 75 mm. Compound leaves with five leaflets: about 140 mm.
- *Attachment*.—Petiolate.

Leaflets:

- *Shape*.—Ovate.
- *Apex*.—Apiculate.
- *Base*.—Attenuate.
- *Margin*.—Serrate.
- *Texture of top surface*.—Glabrous.
- *Texture of bottom surface*.—Mostly glabrous. Hirsute hairs present.
- *Color*.—Young foliage upper side: RHS Green 137A. Young foliage under side: RHS Green 138B. Mature foliage upper side: RHS Green NN137A. Mature foliage under side: RHS Greyed-Green 191A.
- *Venation*.—Type: Pinnate. Venation color upper side: RHS Green-Yellow 145C. Venation color under side: RHS Yellow-Green 145C.

Petiole:

- *Single leaves*.—Length: 8.5 mm. Diameter: 3 mm.
- *Compound leaves*.—Length: 12 to 30 mm. Diameter: 3.5 to 5.5 mm. Color: Upper surface: Greyed-Purple N186C Lower Surface: Greyed-Purple N186C filtered overtop a base of Green 143A
- *Texture*.—Glabrous all surfaces.

Rachis:

- *Length*.—9 to 20 mm.
- *Diameter*.—3.5 to 5.5 mm.
- *Color*.—Upper surface: Greyed-Purple N186C Lower Surface: Greyed-Purple N186C filtered overtop a base of Green 143A
- *Texture*.—Glabrous all surfaces.

FLOWER

Time to flower: Plants begin to bloom around 65 to 70 days after planting, continuously blooming until season ending frost.

Inflorescence and flower type and habit: Fully double waterlily dahlia inflorescence. Upright attitude. Ray florets and disc florets acropetally arranged on a capitulum, forming a double inflorescence.

Post production longevity: Inflorescences maintain good substance on the plant for about 14 days and for about 5 days as a cut flower.

Fragrance: None.

Quantity of Inflorescences: On average 10 to 14 inflorescences and buds at one time.

Inflorescence size:

- *Diameter*.—5.7 cm.
- *Height*.—11.2 cm.
- *Receptacle diameter*.—10.5 mm.

Bud:

- *Shape*.—Oblate.
- *Length*.—14 mm.
- *Diameter*.—20 mm.
- *Color*.—RHS Yellow-Green N144A.
- *Texture*.—Glabrous.

Ray Florets:

- *Number of ray florets per inflorescence*.—About 115 arranged in 10 whorls.

*Length*.—About 46 mm.
*Width*.—About 22.5 mm.
*Shape*.—Obovate.
*Apex*.—Obtuse.
*Base*.—Aequilateral.
*Margin*.—Entire.
*Aspect*.—Most upright, some forward facing.
*Texture and Appearance*.—Upper surface-Smooth, velvety with gold diamond dust reflective qualities Lower surface-Smooth, velvety with gold diamond dust reflective qualities
*Color*.—When opening, upper surface: Greyed-Purple 186A. Stripes Red N45A. When opening, lower surface: Fading blend of Greyed-Orange 163B and Greyed-Purple 186A. Fully opened, upper surface: Picotee edge colored Red N45A Light blend of Greyed-Purple 186B at the apex that filters over 163C and 163D at the base. Stripes Red N45A. Fully opened, lower surface: Heavy pigmentated blend of 186A over 163C Disc Florets:
*Number of disc florets per inflorescence*.—About 45.
*Shape*.—Tubular.
*Apex*.—Acute.
*Margin*.—Entire.
*Length*.—About 9 mm.
*Diameter, base*.—About 1 mm.
*Color*.—Apex Yellow-Orange 21B, midsection N25B, base Yellow-Orange 14B Phyllaries:
*Quantity per inflorescence*.—Average 7 arranged in a single whorl.
*Length*.—About 16 mm.
*Width*.—About 7 mm.
*Shape*.—Rhombic.
*Apex*.—Acute.
*Base*.—Truncate.
*Margin*.—Entire.
*Texture*.—Upper and lower surfaces smooth, glabrous, waxy, marked with grooves.
*Color*.—Upper Surface Green 137B; Lower Surface Green NN137B.

Peduncle:
*Length*.—20 cm.
*Diameter*.—5.5 mm.
*Angle*.—Erect.
*Strength*.—Very good.
*Texture*.—Glabrous.
*Color*.—RHS Greyed-Purple N186C.

REPRODUCTIVE ORGANS

Disc florets:
Stamens:
*Number*.—5.
*Stamen Attachment*.—Filament adnate to ventral surface of corolla.
*Stamen length*.—About 8.5 mm.

Anthers:
*Length*.—About 5.5 mm.
*Width*.—Less than 1 mm.
*Shape*.—Linear.
*Color*.—Yellow-Orange N25D.
*Pollen*.—Quantity: Moderate. Color: Yellow-Orange N25D.

Pistil:
*Number*.—1.
*Length*.—About 22 mm.
*Style Length*.—About 18 mm.
*Style Color*.—Yellow 4D.
*Stigma shape*.—Bifurcate.
*Stigma length*.—About 4 mm.
*Stigma width*.—About 0.5 mm.
*Stigma color*.—Yellow-Orange 21A.
*Ovary*.—Position: Inferior. Shape: Truncate. Length: 2.5 mm. Width: 1.5 mm. Color: RHS Green-White 157A.

OTHER CHARACTERISTICS

Fruit/Seed: About 12 mm long, 2.5 mm wide, colored near Brown 200A.

Disease/pest resistance: Neither resistance nor susceptibility to typical diseases and pests of *Dahlia* has been observed.

Weather and climate performance: Plants of the new Dahlia have resisted wilting and fading of the leaves and inflorescences in field grown conditions. Daylight length has minimal effects on bud and inflorescence production, maintaining cut flower output into late season light and weather conditions.

What is claimed is:

1. A new and distinct cultivar of *Dahlia* plant named 'LeeAnn's WL186B' as herein illustrated and described.

* * * * *